(12) United States Patent
Min et al.

(10) Patent No.: US 10,287,229 B2
(45) Date of Patent: May 14, 2019

(54) METHOD OF CONTINUOUSLY RECOVERING (METH)ACRYLIC ACID

(71) Applicant: LG CHEM, LTD., Seoul (KR)

(72) Inventors: Yoon Jae Min, Daejeon (KR); Se Won Baek, Daejeon (KR); Jong Hun Song, Daejeon (KR); Sul Hee Yoo, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/752,841

(22) PCT Filed: Oct. 17, 2016

(86) PCT No.: PCT/KR2016/011646
§ 371 (c)(1),
(2) Date: Feb. 14, 2018

(87) PCT Pub. No.: WO2017/111277
PCT Pub. Date: Jun. 29, 2017

(65) Prior Publication Data
US 2018/0244601 A1    Aug. 30, 2018

(30) Foreign Application Priority Data

Dec. 22, 2015 (KR) .................. 10-2015-0184161

(51) Int. Cl.
C07C 51/44    (2006.01)
B01D 3/00     (2006.01)
B01D 3/32     (2006.01)

(52) U.S. Cl.
CPC ............. *C07C 51/44* (2013.01); *B01D 3/009* (2013.01); *B01D 3/322* (2013.01)

(58) Field of Classification Search
CPC ......... C07C 51/44; C07C 57/04; B01D 3/009; B01D 3/322
See application file for complete search history.

(56) References Cited

U.S. PATENT DOCUMENTS

| | | | |
|---|---|---|---|
| 4,317,926 A | 3/1982 | Sato et al. | |
| 5,734,075 A | 3/1998 | Fauconet et al. | |
| 5,897,749 A | 4/1999 | Kroker et al. | |
| 6,252,110 B1 * | 6/2001 | Uemura ................ | B01D 3/148 203/39 |
| 6,348,135 B1 | 2/2002 | Nakahara et al. | |
| 6,632,329 B1 | 10/2003 | Mizutani et al. | |
| 6,642,414 B2 | 11/2003 | Mitsumoto et al. | |
| 6,666,956 B1 * | 12/2003 | Nishimura ............ | B01D 3/322 159/27.1 |
| 7,014,736 B2 | 3/2006 | Matsumoto | |
| 7,342,130 B2 | 3/2008 | Shibusawa et al. | |
| 7,388,109 B2 | 6/2008 | Machhammer et al. | |
| 8,308,913 B2 | 11/2012 | Kang et al. | |
| 9,211,484 B2 | 12/2015 | Martin Sanchez et al. | |
| 2008/0183014 A1 | 7/2008 | Diefenbacher et al. | |
| 2009/0253934 A1 | 10/2009 | Ho et al. | |
| 2010/0217030 A1 | 8/2010 | Laux et al. | |
| 2010/0286443 A1 | 11/2010 | Oba | |

FOREIGN PATENT DOCUMENTS

| | | |
|---|---|---|
| CN | 102971057 A | 3/2013 |
| JP | 2861983 B2 | 12/1998 |
| JP | 11012222 A | 1/1999 |
| JP | 2000-239229 A | 9/2000 |
| JP | 2000256258 A | 9/2000 |
| JP | 2001190901 A | 7/2001 |
| JP | 2003-171342 A | 6/2003 |
| JP | 2003192641 A | 7/2003 |
| JP | 2005177633 A | 7/2005 |
| JP | 3918528 B2 | 5/2007 |
| JP | 2009242286 A | 10/2009 |
| JP | 2011504475 A | 2/2011 |
| JP | 5104275 B2 | 12/2012 |
| JP | 5156375 B2 | 3/2013 |
| JP | 2014070069 A | 4/2014 |
| JP | 5715318 B2 | 5/2015 |
| JP | 2015174851 A | 10/2015 |
| KR | 100464841 B1 | 4/2005 |
| KR | 100714631 B1 | 5/2007 |
| KR | 100932467 B1 | 12/2009 |

OTHER PUBLICATIONS

Arneth, et al.: "Characteristics of thermosiphon reboilers", XP004235249, International Journal of Thermal Science, Elsevier, vol. 40, No. 4, Apr. 1, 2001, pp. 385-391.

* cited by examiner

*Primary Examiner* — Yevgeny Valenrod
*Assistant Examiner* — Blaine G Doletski
(74) *Attorney, Agent, or Firm* — Dentons US LLP

(57) ABSTRACT

A method of continuously recovering (meth)acrylic acid is provided. The method of continuously recovering (meth)acrylic acid according to the present disclosure enables use of a natural circulation type of reboiler which does not require an operating part in a destructive distillation process of recovering (meth)acrylic acid from a (meth)acrylic acid waste liquid, and therefore, stable operation of the continuous process may be achieved while simplifying equipment configuration.

3 Claims, 3 Drawing Sheets

[FIG. 1]
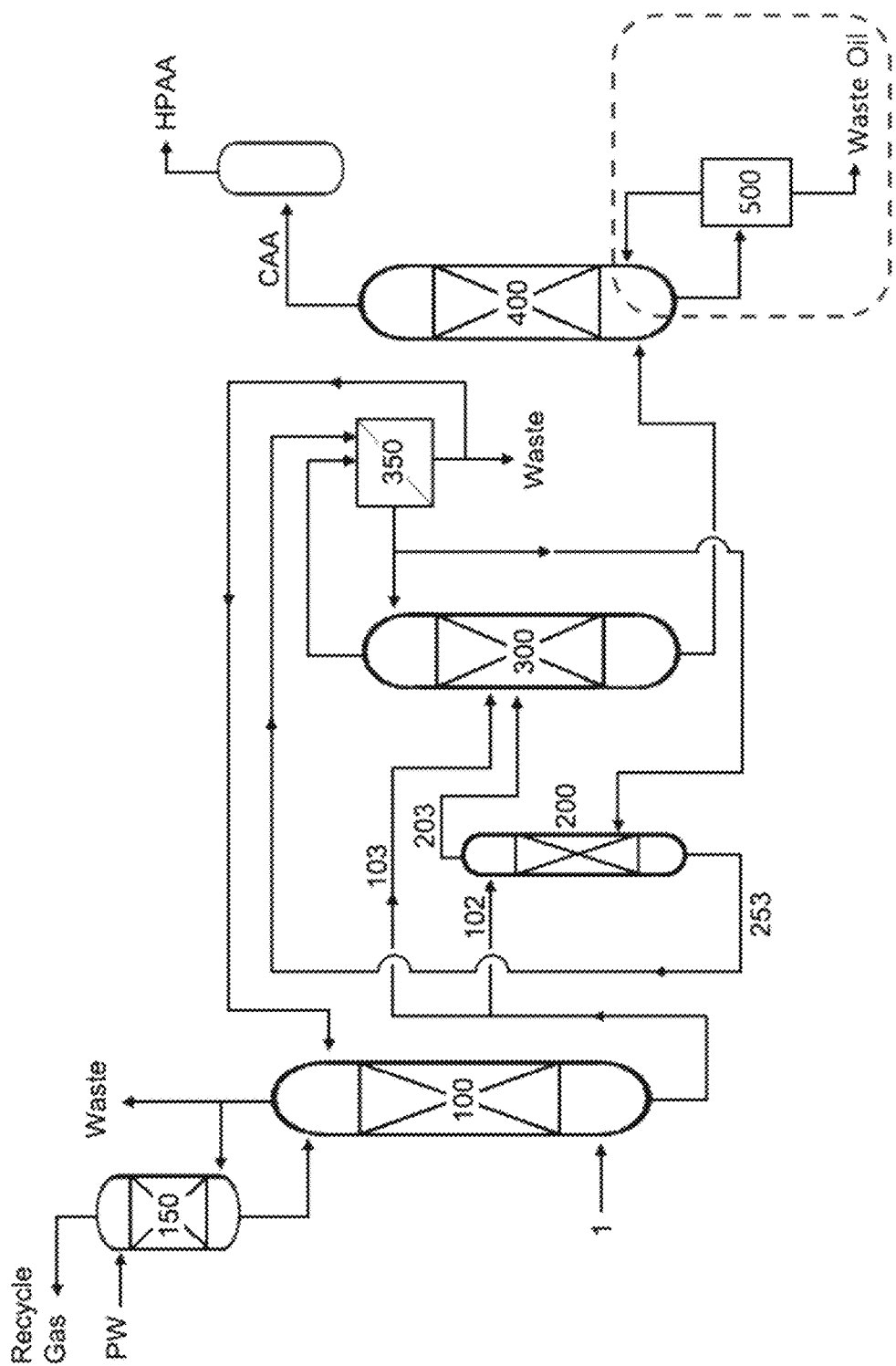

[FIG. 2]
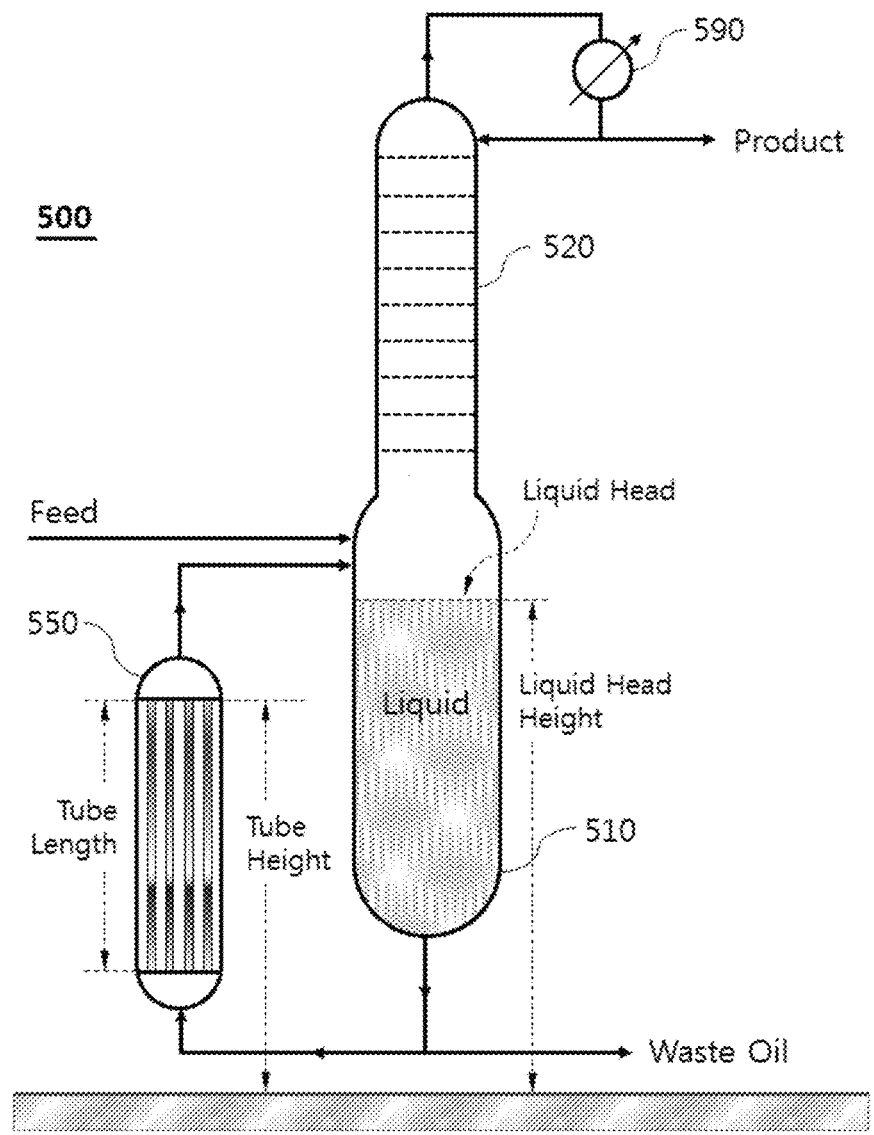

[FIG. 3]
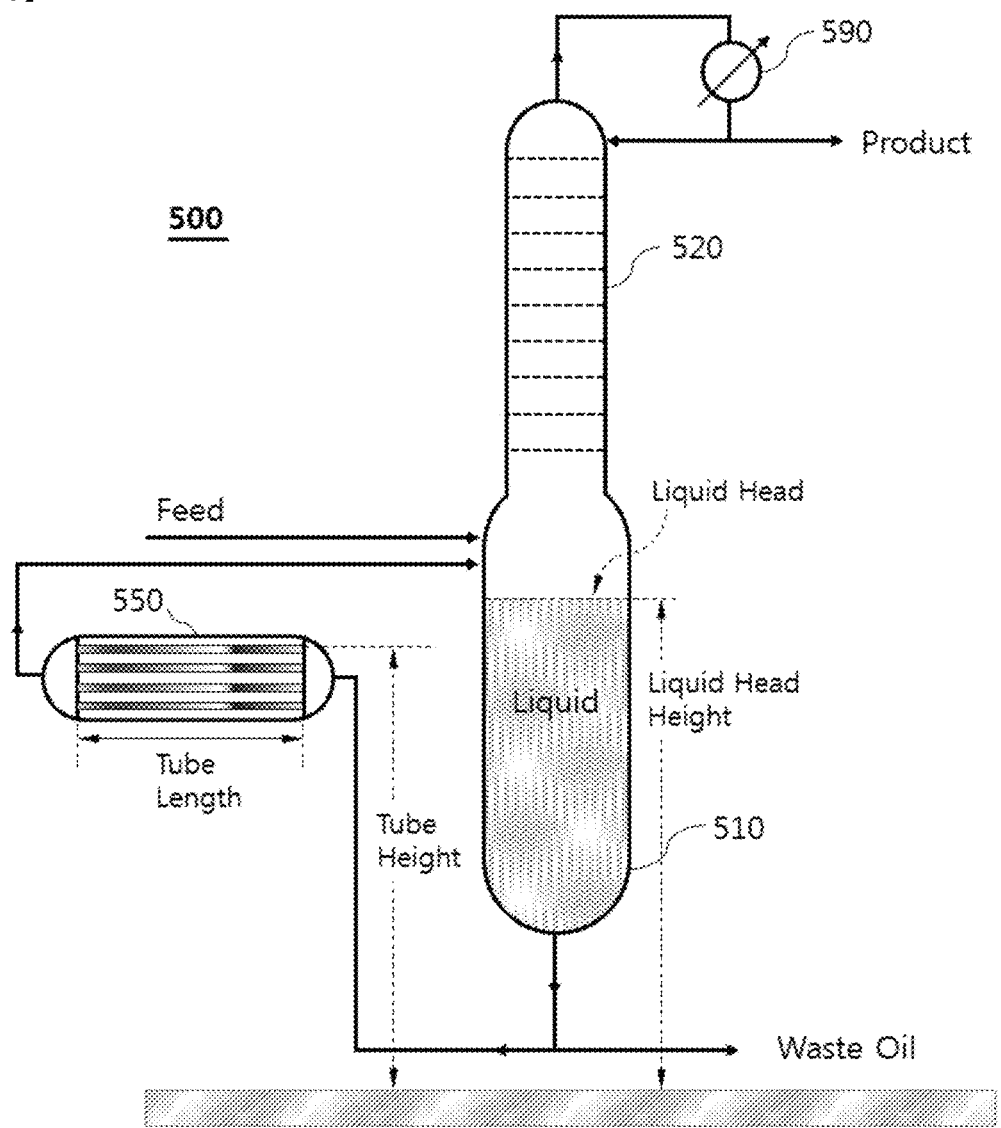

METHOD OF CONTINUOUSLY RECOVERING (METH)ACRYLIC ACID

CROSS-REFERENCE TO RELATED APPLICATION

This application is a National Stage Application of International Application No. PCT/KR2016/011646, filed Oct. 17, 2016, and claims the benefit of Korean Patent Application No. 10-2015-0184161, filed on Dec. 22, 2015, the contents of which are incorporated herein by reference in their entirety for all purposes as if fully set forth below.

TECHNICAL FIELD

The present disclosure relates to a method of continuously recovering (meth)acrylic acid, and more particularly, to a method of continuously recovering (meth)acrylic acid from a (meth)acrylic acid waste liquid including (meth)acrylic acid, (meth)acrylic acid dimers, and high-boiling-point by-products.

BACKGROUND OF ART (Meth)acrylic acid which is a main raw material of a superabsorbent polymer (SAP) is generally obtained by gas-phase oxidation reaction of propylene, etc.

For example, a raw material compound, such as propane, propylene, (meth)acrolein, etc., is subjected to gas-phase oxidation reaction in the presence of a catalyst to obtain a (meth)acrylic acid-containing mixed gas, which is then condensed or absorbed into an absorption solvent and collected as a (meth)acrylic acid-containing solution. From this (meth)acrylic acid-containing solution, low-boiling-point components such as the absorption solvent, (meth)acrylic acid dimers, (meth)acrylic acid oligomers, and high-boiling-point by-products such as maleic acid are separated by a series of purification processes to obtain crude (meth)acrylic acid.

A waste liquid obtained as a waste material in the process of separating the high-boiling-point by-products includes part of unrecovered (meth)acrylic acid, (meth)acrylic acid dimers, and high-boiling-point by-products such as maleic acid which are generated during the purification process.

In particular, it is known that a large amount of the (meth)acrylic acid dimers included in the waste liquid (hereinafter referred to as '(meth)acrylic acid waste liquid') may be recovered as (meth)acrylic acid through a high-temperature or catalytic reaction.

Therefore, disposal of the (meth)acrylic acid waste liquid leads to a loss of (meth) acrylic acid, which is economically disadvantageous. For this reason, a variety of methods of stably recovering (meth)acrylic acid from the (meth)acrylic acid waste liquid have been suggested.

However, there are limitations in that most of the methods require complicated equipment and high energy consumption, and stability of the process operation is still low.

PRIOR ART DOCUMENTS

Patent Document (Patent Document 1) U.S. Pat. No. 6,252,110 B1 (2001 Jun. 26)

DETAILED DESCRIPTION OF THE INVENTION

Technical Problem

The present disclosure provides a method of continuously recovering (meth)acrylic acid which enables stable operation of a continuous process while simplifying equipment configuration of a destructive distillation process of recovering (meth) acrylic acid from a (meth) acrylic acid waste liquid.

Technical Solution

According to the present disclosure, a method of continuously recovering (meth)acrylic acid from a (meth)acrylic acid waste liquid including (meth)acrylic acid, (meth)acrylic acid dimers, and high-boiling-point by-products is provided, wherein the recovering of (meth)acrylic acid is performed in a destructive distillation system 500 including a distillation column including a (meth)acrylic acid waste liquid-receiving section 510 and a distillation section 520 at the top portion thereof, and a natural circulation type of reboiler 550 which is connected to the distillation column and heats a liquid discharged from the lower portion of the distillation column by passing the liquid through a plurality of heat exchanger tubes to supply the liquid to the (meth)acrylic acid waste liquid-receiving section 510 of the distillation column, and the destructive distillation system 500 is operated such that the maximum height of the (meth)acrylic acid waste liquid in the (meth)acrylic acid waste liquid-receiving section 510 corresponds to 85% or more of the height of the top end of the heat exchanger tube of the natural circulation type of reboiler 550.

Hereinafter, a method of continuously recovering (meth) acrylic acid according to embodiments of the present disclosure will be described in more detail.

The terminology used in this description is just for explaining exemplary embodiments, and it is not intended to restrict the present disclosure.

The singular expressions used herein may include the plural expressions unless it is differently expressed contextually. Further, the term "include", when used in this specification, specifies the presence of stated features, regions, integers, steps, operations, elements, or components, but does not preclude the addition of other features, regions, integers, steps, operations, elements, or components.

As used herein, the term '(meth)acrylic acid' means acrylic acid and/or methacrylic acid.

As used herein, the term '(meth)acrylic acid-containing mixed gas' refers to a mixed gas which may be produced during synthesis of (meth)acrylic acid by gas-phase oxidation reaction. As a non-limiting example, the (meth)acrylic acid-containing mixed gas may be obtained by gas-phase oxidation of one or more compounds ('raw material compounds') selected from the group consisting of propane, propylene, butane, isobutylene, and (meth)acrolein in the presence of a catalyst.

The (meth)acrylic acid-containing mixed gas may include (meth)acrylic acid, non-reacted raw material compounds, (meth)acrolein, an inert gas, carbon monoxide, carbon dioxide, water vapor, and various organic by-products (acetic acid, low-boiling-point by-products (light ends), high-boiling-point by-products (heavies), etc.). Here, the 'low-boiling-point by-products' (light ends) or 'high-boiling-point by-products' (heavies) are kinds of by-products that may be generated in the process of preparing and recovering desired (meth)acrylic acid, and generally refer to compounds having a smaller or larger molecular weight than (meth)acrylic acid.

Meanwhile, in a distillation system using a natural circulation type of reboiler, natural circulation may be caused by a density difference due to a temperature gradient between a material (a liquid to be distilled) injected into the reboiler and a material (a liquid-gas mixture produced by heat exchange) discharged from the reboiler.

When this natural circulation type of reboiler is stably operated, an operating part such as a pump is not required, and thus there are advantages that equipment configuration may be simplified and energy consumption may be reduced. In general, the natural circulation type of reboiler is used for a liquid having viscosity of 0.5 cP or less under operating conditions and a low fouling tendency at the inner wall of the heat exchanger tube of the reboiler in the case where a pressure in the reaction system is high.

However, the (meth)acrylic acid waste liquid obtained during the process of preparing (meth)acrylic acid has high viscosity of 20 cP to 60 cP at 100° C. to 150° C., and shows a high fouling tendency at the inner wall of the heat exchanger tube of the reboiler when it is exposed to a high temperature.

Further, when the (meth)acrylic acid waste liquid having high viscosity is applied to the natural circulation type of reboiler, continuous liquid circulation does not occur but a pulse flow occurs. As a result, the temperature inside the reboiler may fluctuate severely, flooding may occur in trays of the distillation column connected to the reboiler, or the system may be operated with some empty trays.

It is known that use of the natural circulation type of reboiler in the distillation of high-viscosity (meth)acrylic acid waste liquid is restricted or practically impossible. Usually, kettle reboilers, fired reboilers, forced circulation reboilers, etc. are used.

However, according to the experimental results of the present inventors, it is possible to use the natural circulation type of reboiler when the system is operated such that the liquid head of the (meth)acrylic acid waste liquid-receiving section corresponds to 85% or more of the height of the top end of the heat exchanger tube equipped inside the natural circulation type of reboiler. Accordingly, equipment configuration for obtaining (meth)acrylic acid from the (meth)acrylic acid waste liquid may be simplified, and stable operation of a continuous process is also possible.

According to an embodiment of the present disclosure, in a method of recovering (meth)acrylic acid from a (meth)acrylic acid waste liquid including (meth)acrylic acid, (meth)acrylic acid dimers, and high-boiling-point by-products, the recovering of (meth)acrylic acid is performed in a destructive distillation system 500 including a distillation column including a (meth)acrylic acid waste liquid-receiving section 510 and a distillation section 520 at the top portion thereof, and a natural circulation type of reboiler 550 which is connected to the distillation column and heats the liquid discharged from the bottom of the distillation column by passing the liquid through a plurality of heat exchanger tubes to supply the liquid to the (meth)acrylic acid waste liquid-receiving section 510 of the distillation column, and the destructive distillation system 500 is operated such that the maximum height of the (meth)acrylic acid waste liquid in the (meth)acrylic acid waste liquid-receiving section 510 corresponds to 85% or more of the height of the top end of the heat exchanger tube of the natural circulation type of reboiler 550.

The present disclosure relates to the method of continuously recovering (meth)acrylic acid from a (meth)acrylic acid waste liquid including (meth)acrylic acid, (meth)acrylic acid dimers, and high-boiling-point by-products by destructive distillation.

As a non-limiting example, FIG. 1 shows an apparatus for preparing (meth)acrylic acid and a process diagram showing an overall flowchart. The (meth)acrylic acid waste liquid is a liquid discharged from the lower part of a high-boiling-point by-product separation column 400.

In other words, the (meth)acrylic acid waste liquid is obtained as waste in the process of separating the high-boiling-point by-products during a series of purification processes of the (meth)acrylic acid-containing solution, and includes part of unrecovered (meth)acrylic acid, and (meth)acrylic acid dimers and high-boiling-point by-products such as maleic acid which are generated during the purification process.

Here, the (meth)acrylic acid-containing solution refers to a solution collected by condensing a (meth)acrylic acid-containing mixed gas or absorbing the (meth)acrylic acid-containing mixed gas into an absorption solvent, in which the (meth)acrylic acid-containing mixed gas is obtained by subjecting a raw material compound such as propane, propylene, (meth)acrolein, etc. to gas-phase oxidation reaction in the presence of a catalyst.

In particular, the (meth)acrylic acid waste liquid includes a large amount of (meth)acrylic acid dimers which are formed during the purification process, and the (meth)acrylic acid dimers may be recovered as (meth)acrylic acid by decomposition through a high-temperature or catalytic reaction.

FIGS. 2 and 3 show a destructive distillation system which is used for continuous recovery of (meth)acrylic acid from the (meth)acrylic acid waste liquid and a process diagram showing a flowchart according to embodiments of the present disclosure, respectively.

According to embodiments of the present disclosure, the recovery of (meth)acrylic acid may be performed in the destructive distillation system 500 including a distillation column including a (meth)acrylic acid waste liquid-receiving section 510 and a distillation section 520 at the top portion thereof, and a natural circulation type of reboiler 550 which is connected to the distillation column and heats the liquid discharged from the lower portion of the distillation column by passing the liquid through a plurality of heat exchanger tubes to supply the liquid to the (meth)acrylic acid waste liquid-receiving section 510 of the distillation column.

Particularly, in the destructive distillation system 500, the (meth)acrylic acid waste liquid as a feed is supplied to the distillation column and received in the (meth)acrylic acid waste liquid-receiving section 510 at an arbitrary liquid level.

The (meth)acrylic acid waste liquid-receiving section 510 is maintained at a temperature level at which the thermal decomposition of the (meth)acrylic acid waste liquid may occur. For example, the destructive distillation system 500 may be operated such that the temperature of the (meth)acrylic acid waste liquid-receiving section 510 is maintained at 100° C. to 200° C., and preferably 130° C. to 180° C. This temperature control may be performed by supplying a heating medium, which is heated to a predetermined level by an external heat circulator, to a jacket of the (meth)acrylic acid waste liquid-receiving section 510.

While the (meth)acrylic acid waste liquid supplied from the lower portion of the distillation column to the natural circulation type of reboiler 550 passes through a plurality of heat exchanger tubes which are equipped inside the natural circulation type of reboiler 550, heat exchange occurs.

The (meth)acrylic acid waste liquid in a liquid-gas mixture state by the heat exchange is supplied to the (meth) acrylic acid waste liquid-receiving section 510 of the distillation column.

A liquid phase in the liquid-gas mixture is put to the (meth)acrylic acid waste liquid-receiving section 510 again, while a gas phase is distilled through the distillation section 520, and a part thereof is discharged from the top portion of the distillation column. The gas phase discharged from the top portion of the distillation column is condensed into a liquid phase in a condenser 590, while a part thereof is refluxed to the top portion of the distillation column, and the rest is obtained as a final product, (meth)acrylic acid.

The destructive distillation of the (meth)acrylic acid waste liquid is continuously performed.

In particular, according to embodiments of the present disclosure, the destructive distillation system 500 is operated such that the maximum height of the (meth)acrylic acid waste liquid in the (meth)acrylic acid waste liquid-receiving section 510 corresponds to 85% or more of the height of the top end of the heat exchanger tube of the natural circulation type of reboiler 550.

Here, the height of the top end of the heat exchanger tube of the natural circulation type of reboiler 550 means a vertical distance from any reference point (for example, the ground) to the top end of the heat exchanger tube equipped inside the natural circulation type of reboiler 550, in the natural circulation type of reboiler 550 connected to the distillation column.

For example, in the case of the natural circulation type of reboiler 550 equipped with the heat exchanger tube in a vertical direction with respect to the ground as in the destructive distillation system 500 of FIG. 2, the height of the top end of the heat exchanger tube means a vertical distance from the ground to the top end (outlet portion) of the heat exchanger tube.

Further, in the case of the natural circulation type of reboiler 550 equipped with the heat exchanger tube in a horizontal direction with respect to the ground as in the destructive distillation system 500 of FIG. 3, the height of the top end of the heat exchanger tube means a distance from the ground to the heat exchanger tube located vertically farthest from the ground.

The maximum height of the (meth)acrylic acid waste liquid in the (meth)acrylic acid waste liquid-receiving section 510 means a vertical distance from any reference point to the liquid head of the (meth)acrylic acid waste liquid-receiving section 510.

According to the present disclosure, operating conditions of the above-described destructive distillation system 500 enables stable use of the natural circulation type of reboiler 550 which does not require an operating part in the destructive distillation process of recovering (meth)acrylic acid from the (meth)acrylic acid waste liquid.

Preferably, the destructive distillation system 500 is operated such that the maximum height of the (meth)acrylic acid waste liquid in the (meth)acrylic acid waste liquid-receiving section 510 corresponds to 85% or more, 90% or more, 94% or more, 95% or more, 100% or more, 104% or more, 105% or more, 110% or more, 114% or more, 115% or more, 120% or more, 150% or more, 85% to 150%, 85% to 120%, 90% to 115%, or 94% to 114% of the height of the top end of the heat exchanger tube of the natural circulation type of reboiler 550.

In other words, to enable the use of the natural circulation type of reboiler (550) in the destructive distillation process of recovering (meth)acrylic acid from the (meth)acrylic acid waste liquid, the destructive distillation system 500 should be operated such that the maximum height of the (meth) acrylic acid waste liquid in the (meth)acrylic acid waste liquid-receiving section 510 corresponds to 85% or more of the height of the top end of the heat exchanger tube of the natural circulation type of reboiler 550, and as the ratio is higher, natural circulation may be more stably maintained.

The ratio of the height may be determined by considering a feed inlet height of the distillation column, a volume of the (meth)acrylic acid waste liquid-receiving section 510 in the distillation column, an installation height of the natural circulation type of reboiler 550, a kind of the natural circulation type of reboiler 550, etc.

According to embodiments of the present disclosure, when the destructive distillation system 500 is operated under the above-described conditions, natural and stable circulation of the (meth)acrylic acid waste liquid by the natural circulation type of reboiler is possible.

Stable circulation of the (meth)acrylic acid waste liquid in the destructive distillation system 500 may be confirmed by temperature profiles in the distillation section 520 of the distillation column, flooding in the trays of the distillation column 520, a temperature fluctuation width at each point inside the natural circulation type of reboiler 550, etc.

For example, the temperature fluctuation width inside the heat exchanger tube which is measured at points corresponding to 25%, 50%, 75%, and 100% in the longitudinal direction of the heat exchanger tube of the natural circulation type of reboiler 550 may be as narrow as 4.5° C. or less, 4° C. or less, 2° C. or less, or 1° C. or less, respectively.

In contrast, when a pulse flow occurs due to unstable circulation in the reboiler, the temperature fluctuation width becomes large at each point inside the reboiler, temperature profiles in the distillation section 520 are unstable, or the system is operated with some empty trays, i.e., continuous operation is impossible.

Meanwhile, according to embodiments of the present invention, as the natural circulation type of reboiler 550, those having any configuration known in the art to which the present invention pertains may be used without particular limitation.

Preferably, the natural circulation type of reboiler 550 may be a vertical thermosiphon reboiler as in FIG. 2, or a horizontal thermosiphon reboiler as in FIG. 3.

The vertical thermosiphon reboiler may be more preferably used because it enables more stable natural circulation of high-viscosity (meth)acrylic acid waste liquid.

The distillation section 520 of the distillation column may be a multistage tray column with a perforated plate, and preferably, a sieve tray column or a dual-flow tray column.

The (meth)acrylic acid which is obtained as a final product through the above-described processes may be recycled to a high-boiling-point by-product separation column to be recovered as crude (meth)acrylic acid, or to be obtained as (meth)acrylic acid with high purity through an additional crystallization process.

Advantageous Effects

A method of continuously recovering (meth)acrylic acid according to the present disclosure enables use of a natural circulation type of reboiler which does not require an operating part in a destructive distillation process of recovering (meth)acrylic acid from a (meth)acrylic acid waste liquid, and therefore, stable operation of the continuous process may be achieved while simplifying equipment configuration.

BRIEF DESCRIPTION OF THE DRAWINGS

FIG. 1 shows an apparatus for preparing (meth)acrylic acid and a process diagram showing an overall flowchart; and FIGS. 2 and 3 each show a destructive distillation system which is used for continuous recovery of (meth)acrylic acid from a (meth)acrylic acid waste liquid and a process diagram showing a flowchart.

REFERENCE NUMERALS

500: Destructive distillation system
510: (Meth)acrylic acid waste liquid-receiving section
520: Distillation section
550: Natural circulation type of reboiler
590: Condenser
1: (Meth)acrylic acid-containing mixed gas
100: (Meth)acrylic acid absorption tower
102: (Meth)acrylic acid aqueous solution transfer line
150: Acetic acid absorption tower
200: (Meth)acrylic acid extraction column
203: Extract transfer line
253: Filtrate transfer line
300: Distillation column
350: Phase separation tank
400: High boiling point by-product separation column
CAA: Crude (meth)acrylic acid
HPAA: High-purity (meth)acrylic acid

DETAILED DESCRIPTION OF THE EMBODIMENTS

Hereinafter, preferred examples are provided for better understanding. However, these examples are for illustrative purposes only, and the present invention is not intended to be limited by these examples.

Example 1

A destructive distillation system 500 equipped with a distillation column consisting of a (meth)acrylic acid waste liquid-receiving section 510 having an inner diameter of 7 cm and a height of 100 cm and a distillation section 520 including a total of 9 dual-flow trays having an inner diameter of 3 cm, a tray spacing of 10 cm, and a tray opening ratio of 14%, and a natural circulation type of reboiler 550 having an inner diameter of 1 inch and a height of 100 cm was prepared as in FIG. 2.

A temperature of an indirect heat exchange medium flowing into the outer space of the natural circulation type of reboiler 550 was 175° C., and a pressure at the top end of the distillation column was 50 torr.

A distillate discharged from the upper portion of the distillation section 520 was condensed into a liquid phase through a condenser 590, and 50% by weight of the condensed liquid phase was refluxed into the upper portion of the distillation section 520. As a result, a reflux ratio was 1.0, and the rest thereof was discharged as a final product.

The destructive distillation system 500 was operated such that the maximum height of the (meth)acrylic acid waste liquid in the (meth)acrylic acid waste liquid-receiving section 510 was maintained at 114% of the height of the top end of the heat exchanger tube of the natural circulation type of reboiler 550.

Inner temperatures of the heat exchanger tube were measured at points corresponding to 25%, 50%, 75%, and 100% in the longitudinal direction of the heat exchanger tube of the natural circulation type of reboiler 550, and are shown in the following Table 1.

As a result, the (meth)acrylic acid waste liquid was continuously circulated by the natural circulation type of reboiler 550, the temperature fluctuation width at each point inside the reboiler was 0.4° C. to 0.8° C., and a temperature profile of the distillation section was stably maintained throughout the operation time.

Example 2

Operation was performed in the same manner as in Example 1, except that the destructive distillation system 500 was operated such that the maximum height of the (meth)acrylic acid waste liquid in the (meth)acrylic acid waste liquid-receiving section 510 was maintained at 104% of the height of the top end of the heat exchanger tube of the natural circulation type of reboiler 550.

Inner temperatures of the heat exchanger tube were measured at points corresponding to 25%, 50%, 75%, and 100% in the longitudinal direction of the heat exchanger tube of the natural circulation type of reboiler 550, and are shown in the following Table 1.

As a result, the (meth)acrylic acid waste liquid was continuously circulated by the natural circulation type of reboiler 550, the temperature fluctuation width at each point inside the reboiler was 0.5° C. to 1.8° C., and a temperature profile of the distillation section was stably maintained throughout the operation time.

Example 3

Operation was performed in the same manner as in Example 1, except that the destructive distillation system 500 was operated such that the maximum height of the (meth)acrylic acid waste liquid in the (meth)acrylic acid waste liquid-receiving section 510 was maintained at 94% of the height of the top end of the heat exchanger tube of the natural circulation type of reboiler 550.

Inner temperatures of the heat exchanger tube were measured at points corresponding to 25%, 50%, 75%, and 100% in the longitudinal direction of the heat exchanger tube of the natural circulation type of reboiler 550, and are shown in the following Table 1.

As a result, the (meth)acrylic acid waste liquid was continuously circulated by the natural circulation type of reboiler 550, the temperature fluctuation width at each point inside the reboiler was 1° C. to 4.2° C., and a temperature profile of the distillation section was stably maintained throughout the operation time.

Comparative Example 1

Operation was performed in the same manner as in Example 1, except that the destructive distillation system 500 was operated such that the maximum height of the (meth)acrylic acid waste liquid in the (meth)acrylic acid waste liquid-receiving section 510 was maintained at 84% of the height of the top end of the heat exchanger tube of the natural circulation type of reboiler 550.

Inner temperatures of the heat exchanger tube were measured at the point corresponding to 25%, 50%, 75%, and 100% in the longitudinal direction of the heat exchanger tube of the natural circulation type of reboiler 550, and are shown in the following Table 1.

As a result, the (meth)acrylic acid waste liquid was discontinuously circulated while showing a pulse flow. As a result, the temperature of the waste liquid in the (meth) acrylic acid waste liquid-receiving section 510 was decreased to 130° C. or lower, and an inner temperature of the heat exchanger tube, which was measured at the point corresponding to 25% in the longitudinal direction of the heat exchanger tube of the natural circulation type of reboiler 550, showed a fluctuation from 130.7° C. to 161.9° C. and stable operation of the destructive distillation process was not achieved. Further, a temperature profile of the distillation section 520 showed unstable patterns, and the system was operated with some empty trays.

TABLE 1

| | | Temperature at each point of tube inside reboiler | | | |
|---|---|---|---|---|---|
| | | 100% point | 75% point | 50% point | 25% point |
| Example 1 | Maximum | 137.6 | 143.3 | 156.2 | 141.4 |
| | Average | 137.4 | 143.0 | 155.8 | 141.0 |
| | Minimum | 137.2 | 142.6 | 155.4 | 140.6 |
| | Fluctuation width | 0.4 | 0.7 | 0.8 | 0.8 |
| Example 2 | Maximum | 141.2 | 147.0 | 155.9 | 145.8 |
| | Average | 141.0 | 146.6 | 155.5 | 144.9 |
| | Minimum | 140.7 | 146.1 | 155.0 | 144.0 |
| | Fluctuation width | 0.5 | 0.9 | 0.9 | 1.8 |
| Example 3 | Maximum | 146.1 | 150.5 | 157.9 | 148.5 |
| | Average | 145.6 | 149.9 | 157.3 | 146.4 |
| | Minimum | 145.1 | 149.2 | 156.7 | 144.3 |
| | Fluctuation width | 1 | 1.3 | 1.2 | 4.2 |

TABLE 1-continued

| | | Temperature at each point of tube inside reboiler | | | |
|---|---|---|---|---|---|
| | | 100% point | 75% point | 50% point | 25% point |
| Comparative Example 1 | Maximum | 153.5 | 158.0 | 164.3 | 161.9 |
| | Average | 151.6 | 155.8 | 159.1 | 146.3 |
| | Minimum | 149.6 | 153.5 | 153.8 | 130.7 |
| | Fluctuation width | 3.9 | 4.5 | 10.5 | 31.2 |

The invention claimed is:

1. A method of continuously recovering (meth)acrylic acid from a (meth)acrylic acid waste liquid including (meth) acrylic acid, (meth)acrylic acid dimers, and high-boiling-point by-products,
wherein the recovering of (meth)acrylic acid is performed in a destructive distillation system including a distillation column including a (meth)acrylic acid waste liquid-receiving section and a distillation section at the top portion thereof, and a natural circulation type of reboiler which is connected to the distillation column and heats the liquid discharged from the lower portion of the distillation column by passing the liquid through a plurality of heat exchanger tubes to supply the liquid to the (meth)acrylic acid waste liquid-receiving section of the distillation column, and
the destructive distillation system is operated such that the maximum height of the (meth)acrylic acid waste liquid in the (meth)acrylic acid waste liquid-receiving section corresponds to 85% to 100% or more of the height of the top end of the heat exchanger tube of the natural circulation type of reboiler.

2. The method of continuously recovering (meth)acrylic acid of claim 1, wherein a temperature fluctuation width inside the heat exchanger tube which is measured at points corresponding to 25%, 50%, 75%, and 100% in the longitudinal direction of the heat exchanger tube of the natural circulation type of reboiler is 4.5° C. or less, respectively.

3. The method of continuously recovering (meth)acrylic acid of claim 1, wherein the natural circulation type of reboiler is a vertical thermosiphon reboiler or a horizontal thermosiphon reboiler.

* * * * *